United States Patent [19]
Ueda et al.

[11] Patent Number: 5,949,080
[45] Date of Patent: Sep. 7, 1999

[54] IRRADIATION APPARATUS FOR EFFECTIVELY PERFORMING INTERMITTENT IRRADIATION IN SYNCHRONISM WITH RESPIRATION

[75] Inventors: Hisaki Ueda, Kashiwa; Masatoshi Nishimura, Misato, both of Japan

[73] Assignee: Hitachi Medical Corporation, Tokyo, Japan

[21] Appl. No.: 08/895,921

[22] Filed: Jul. 17, 1997

[30] Foreign Application Priority Data

Jul. 18, 1996 [JP] Japan ................................ 8-189281

[51] Int. Cl.$^6$ ................................ H01J 37/302
[52] U.S. Cl. ................................ 250/492.3; 378/65
[58] Field of Search ................................ 250/492.3, 398, 250/396 ML; 378/65, 95

[56] References Cited

U.S. PATENT DOCUMENTS

| | | | |
|---|---|---|---|
| 4,031,884 | 6/1977 | Henzel | 378/95 |
| 4,442,352 | 4/1984 | Brahme | 250/398 |
| 4,726,046 | 2/1988 | Nunan | 250/492.1 |
| 4,870,287 | 9/1989 | Cole et al. | 250/398 |
| 4,994,965 | 2/1991 | Crawford et al. | 378/95 |
| 5,012,111 | 4/1991 | Ueda | 250/492.3 |
| 5,017,789 | 5/1991 | Young et al. | 250/396 ML |
| 5,764,723 | 6/1998 | Weinberger et al. | 378/65 |

OTHER PUBLICATIONS

Japanese Journal of Irradiation of Medicine, vol.47, No. 3, pp.44–52, 1987.

*Primary Examiner*—Bruce C. Anderson
*Attorney, Agent, or Firm*—Antonelli, Terry, Stout & Kraus, LLP

[57] ABSTRACT

An irradiation apparatus for treating a treated body by irradiating an electron beam of high energy or the like on the foci of the treated body includes, in order to efficiently and stably performing intermittent irradiation in synchronism with respiration, a respiration synchronizing circuit for detecting a respiration state of a treated body, outputting an irradiation permission signal in synchronism with a rest period of foci which are moved by a respiration motion and outputting an irradiation prohibition signal during other periods and a beam passage change control circuit for deflecting the electron beam or the like from a correct therapy passage, causing the electron beam or the like to impinge upon a predetermined beam stopper portion during a period in which the irradiation prohibition signal is outputted from the respiration synchronizing circuit and returning the electron beam or the like to the correct therapy passage during the period in which the irradiation permission signal is outputted from the respiration synchronizing circuit.

10 Claims, 3 Drawing Sheets

IRRADIATION APPARATUS FOR EFFECTIVELY PERFORMING INTERMITTENT IRRADIATION IN SYNCHRONISM WITH RESPIRATION

BACKGROUND OF THE INVENTION

The present invention relates to an irradiation apparatus such as a microtron or linear accelerator (lineac) for treating a treated body by irradiating the foci of a treated body with beams of charged particles or radiation beams of high energy.

In the radiation therapy, it is important to irradiate only the focus with charged particles beams or radiation beams while the radiation exposure of a normal tissue around the focus is suppressed as much as possible. In that sense, it is significant to use an irradiation synchronized with respiratory cycle. The irradiation synchronized with respiratory cycle is one such that the above-mentioned charged particles beams or radiation beams are irradiated on the focus in synchronism with a rest period of a focus which is being moved by a respiratory movement. According to the irradiation synchronized with respiratory cycle, there can be carried out a more ideal radiation therapy as compared with a general irradiation method in which a focus is irradiated while an irradiation field is widened so as to cover all ranges in which the foci are being moved.

Heretofore, such an irradiation synchronized with respiratory cycle has been described in "Study of Irradiation Synchronized with Respiratory Cycle" (written by Kiyoshi Ohhara, et al.: Japanese Journal of Irradiation in Medicine, Vol. 47, No. 3, pp. 44 to 52, 1987). According to this irradiation synchronized with respiratory cycle, intermittent irradiation is performed in synchronism with respiration by turning on and off a microwave oscillator such as a magnetron or a klystron for exciting the acceleration potential.

However, according to the above-mentioned conventional technology, when this technology is applied to the microtron and the lineac, a delay of irradiation occurs in a respiration synchronizing signal due to a time delay without a reproducibility produced until an oscillator reaches an original microwave output immediately after the oscillator is energized. As a result, it is not possible to perform intermittent irradiation in synchronism with respiration. Also, when this technology is applied to the lineac, energy the charged particle beam is determined depending on, in particular, a microwave output and an electron gun output so that energy of the electron beam becomes unstable. Besides, since such delay of irradiation (unstable intermittent irradiation in synchronism with respiration) occurs, the energy becomes unstable at every respiration. There is then presented the problem that they are accumulated with a lapse of time and become much more remarkable.

SUMMARY OF THE INVENTION

It is an object of the present invention to provide an irradiation apparatus which can stably perform intermittent irradiation in synchronism with respiration without a delay of time in synchronism with a respiration synchronizing signal (irradiation permission/prohibition signal) and which can output beams of charged particles or radiation beams of stable energy when it is applied to the lineac.

The aforesaid object can be attained by an irradiation apparatus which can treat the foci of a treated body by irradiating beams of charged particles or radiation beams of high energy on the foci of the treated body. This irradiation apparatus includes a respiration synchronizing circuit for detecting a respiration state of the treated body, outputting an irradiation permission signal in synchronism with a rest period of the foci which are being moved by a respiration motion and outputting an irradiation prohibition signal during other periods and a beam passage change control circuit for causing the above-mentioned beam to impinge upon a predetermined beam stopper portion out of a correct therapy passage during a period in which the irradiation prohibition signal is outputted from the respiration synchronizing circuit and returning the above-mentioned beam to the correct therapy passage during a period in which the irradiation permission signal is outputted from the respiration synchronizing circuit.

The respiration synchronizing circuit detects the respiration state of the treated body, outputs the irradiation permission signal in synchronism with the rest period of the foci which are being moved by the respiration motion and outputs the irradiation prohibition signal during other periods. The beam passage change control circuit causes the beam to impinge upon the predetermined beam stopper portion out of the correct therapy passage during the period in which the irradiation prohibition signal is outputted from the respiration synchronizing circuit, and returns the beams to the correct therapy passage during the period in which the irradiation permission signal is outputted from the respiration synchronizing circuit, thereby performing the intermittent irradiation in synchronism with respiration. Apart from whether or not the beam is on the correct therapy passage, the beam is being continuously outputted in the inside. Therefore, when the irradiation prohibition signal is switched to the irradiation permission signal (when the beam irradiation is energized) or vice versa (when the beam irradiation is de-energized), the irradiation prohibition signal is switched to the irradiation permission signal or vice versa instantly without a delay of time, thereby making it possible to stably perform the intermittent irradiation in synchronism with respiration. In particular, when this irradiation apparatus is applied to the lineac, there can be outputted beams of charged particles or radiation beams of stable energy.

Although the beam is deflected from the correct therapy passage during a period in which the irradiation prohibition signal is outputted from the respiration synchronizing circuit, the beam is not only deflected from the correct therapy passage but also is caused to strike the predetermined beam stopper portion, resulting in the energy of the beam being consumed and absorbed. Therefore, the irradiation apparatus can be protected from a bad influence exerted when the beam is deflected from the correct passage.

Incidentally, when the beam is caused to impinge upon the beam stopper portion, if the portion where the beam impinge upon the beam stopper portion is properly fluctuated by the beam passage change control circuit, then the impingement of beam can be prevented from being concentrated on one portion with the result that a temperature can be prevented from increasing locally. Thus, a life span of the beam stopper portion can be prolonged, and the irradiation apparatus can be increased in durability and made highly reliable.

As described above, according to the present invention, the intermittent irradiation is performed in synchronism with respiration under the condition that the beam is being outputted in the inside continuously. Therefore, when the beam irradiation is energized or when the beam irradiation is de-energized, the irradiation permission signal is stably switched to the irradiation prohibition signal or vice versa instantly without a delay of time. There is then achieved the effect that the intermittent irradiation can be stably performed in synchronism with respiration. Also, when this irradiation apparatus is applied to the lineac, there is then achieved the effect that beams of charged particles or radiation beams of stable energy can be outputted.

DESCRIPTION OF THE PREFERRED EMBODIMENTS

Embodiments of the present invention will hereinafter be described with reference to the drawings.

Figure 1:
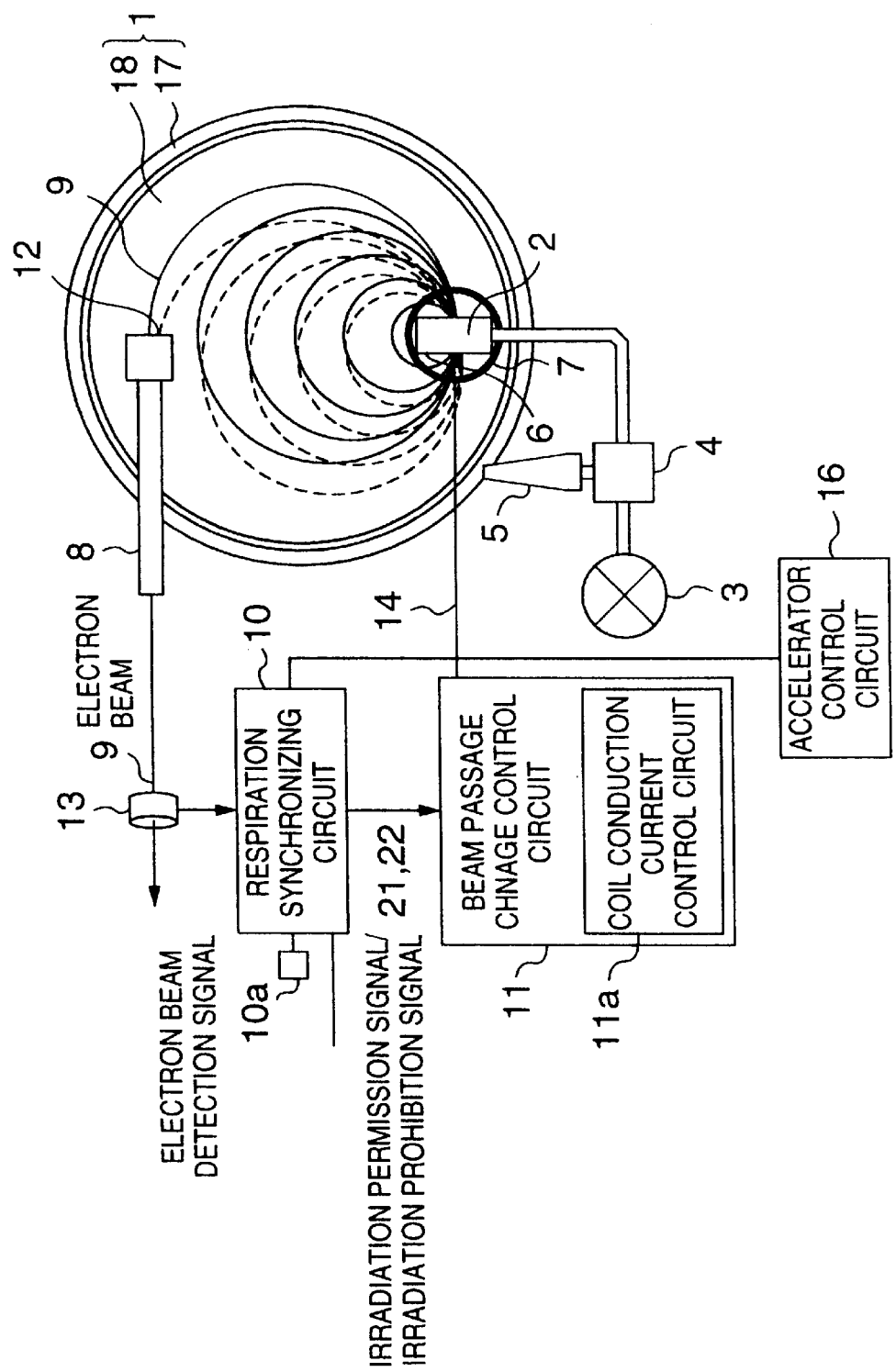
FIG. 1 is a block diagram showing an irradiation apparatus according to an embodiment of the present invention.

FIG. 1 is a block diagram showing an irradiation apparatus according to an embodiment of the present invention. Here, there is illustrated the case that the present invention is applied to a microtron.

The microtron is an accelerator which accelerates electrons in a uniform magnetic field while the electrons are being moved in a circular motion. As shown in FIG. 1, the microtron mainly comprises an electromagnet 1, a cavity resonator 2, a magnetron 3, a circulator 4, an antireflection terminal device 5, an electron gun 6, a circular trim coil 7 and an accelerator control circuit 16. The electromagnet 1 comprises a coil 17 and a disk-like magnetic pole 18.

The magnetron 3 generates a microwave, and the microwave is supplied through the circulator 4 to the cavity resonator 2. A part of microwaves which are not consumed becomes a reflected wave and then returned. The reflected wave is supplied to the antireflection terminal device 5 by the circulator 4, in which it is converted to heat. Such microwave circuit (the cavity resonator 2, the magnetron 3, the circulator 4 and the antireflection terminal device 5) excites an electric field in the inside of the cavity resonator 2.

An electron that is emitted from the electron gun 6 are entered into the cavity resonator 2 and accelerated by an electric field generated within the cavity resonator 2. The electron (electron beam 9) thus accelerated is circularly moved within the uniform electric field generated by the electromagnet 1 and returned to the cavity resonator 2, in which it is accelerated again. The electron beam 9 is repeatedly circularly moved and accelerated until it reaches an extraction pipe 8.

The extraction pipe 8 is made of an iron which shields magnetism, and disposed on a tangent of the circular passage of the electron beam 9 thereby to supply the electron beam 9 of high energy to the outside. In actual practice, the circular passage is inclined due to the influence of accuracy of respective assemblies and accuracy required in the assembly. The circular trim coil 7 is provided as a correction coil for correcting such inclination of the circular passage. By properly energizing the circular trim coil 7, the circular passage of the electron beam 9 is corrected and the electron beam 9 is properly supplied to the outside by the extraction pipe 8. The degree of correction is controlled by a current which energizes the circular trim coil 7.

The electron beam 9 outputted to the outside is directly irradiated on the foci of the patient or introduced into an X-ray generating target (not shown) to generate X-rays. A beam which results from converging the X-rays is irradiated on the foci of the patient.

The irradiation apparatus thus described so far is not particularly different from the conventional apparatus. In addition to the above-mentioned configuration, the irradiation apparatus according to the present invention includes a respiration synchronizing circuit 10 and a beam passage change control circuit 11. The respiration synchronizing circuit 10 detects a respiration state of a treated body (not shown) by a sensor 10a, outputs an irradiation permission signal 21 in synchronism with a rest period (generally, a respiration stop period temporarily occurred from the end of respiration to the beginning of respiration) of the foci of the treated body which is moved by the respiration motion, and outputs an irradiation prohibition signal 22 during other periods. The beam passage change control circuit 11 causes the electron beam 9 to impinge upon a beam stopper portion 12 out of the correct passage as shown by broken lines during a period in which the irradiation prohibition signal 22 is outputted from the respiration synchronizing circuit 10, and returns the beam to the correct passage as shown by solid lines during a period in which the irradiation permission signal 21 is outputted from the respiration synchronizing circuit 10.

In this case, the above-mentioned sensor 10a is comprised of a strain gage attached to the abdomen of the treated body to detect a motion of the abdomen or a pressure sensor for detecting respiration or respiration pressure of the treated body and the like. The beam passage change control circuit 11 includes a coil conduction current control circuit 11a and the above-mentioned circular trim coil 7. The coil conduction current control circuit 11a considerably changes the passage of the accelerated electron beam 9 by increasing the current of the circular trim coil 7 during the period in which the irradiation prohibition signal 22 is outputted from the respiration synchronizing circuit 10 to thereby cause the electron beam to impinge upon the beam stopper portion 12 set at the predetermined position of the extraction pipe 8, thus preventing the electron beam 9 from being outputted to the outside. During the period in which the irradiation permission signal is outputted from the respiration synchronizing circuit, the coil conduction current control circuit returns the current of the circular trim coil 7 to the original low value to thereby cause the electron beam 9 to return to the correct treatment passage so that the electron beam is outputted to the outside. This coil conduction current control circuit 11a may be replaced with a conduction current control circuit of the circular trim coil 7 which corrects the circular passage of the electron beam 9 or a main control circuit or the like (not shown) which includes the conduction current control circuit. While the inlet portion of the extraction pipe 8 is set as the beam stopper portion 12 as described above, such a variant is also possible that a substance different from the extraction pipe 8 may be provided at the inlet portion of the extraction pipe 8 and served as the beam stopper portion 12. As the beam stopper portion 12 in this case, there may be used graphite or the like having high heat-resistance property and which generates less bremsstrahlung radiant rays.

Reference numeral 13 denotes a current transformer which detects a presence or absence of the electron beam 9 outputted from the extraction pipe 8. The current transformer and the respiration synchronizing circuit 10 constitute an interlock circuit. Specifically, the current transformer 13 causes the respiration synchronizing circuit 10 to output an interlock signal when the electron beam 9 is detected during the period in which the respiration synchronizing circuit 10 outputs the irradiation prohibition signal 22, and supplies the interlock signal to an accelerator control circuit 16. As a result, the driving of the microtron is stopped by immediately stopping the electron discharge operation of the electron gun 6 and the oscillation operation of the magnetron 3. The interlock circuit may include the current transformer 13 and a circuit different from the respiration synchronizing circuit 10 which outputs the interlock signal based on the electron beam detection signal from the current transformer 13 and the irradiation prohibition signal 22 from the respiration synchronizing circuit 10.

An operation of the above-mentioned apparatus according to the present invention will be described with reference to also FIGS. 2A to 2C.

Figure 2:
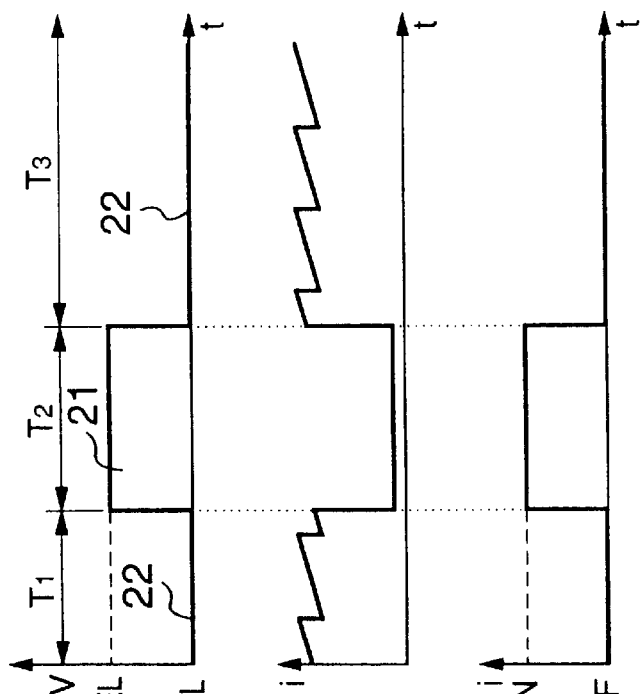
FIGS. 2A to 2C are diagrams of waveforms of signals in the respective portions of the above-mentioned irradiation apparatus.

The respiration synchronizing circuit 10 detects the respiration state of the treated body by the sensor 10a, outputs the irradiation permission signal 21 in synchronism with the rest period of the foci of the treated body, and outputs the irradiation prohibition signal 22 during other periods (FIG. 2A). The coil conduction current control circuit 11a which mainly comprises the beam passage change control circuit 11 increases the current of the circular trim coil 7 during a period (T1) in which the irradiation prohibition signal 22 is outputted from the respiration synchronizing circuit 10 (see FIG. 2B). Thus, the electron beam 9 is considerably changed in passage, caused to impinge upon the beam stopper portion 12 of the extraction pipe 8, and then stopped from being outputted to the outside (see FIG. 2C). The energy of the electron beam 9 is consumed and absorbed when the electron beam impinges upon the beam stopper portion 12.

When the signal from the respiration synchronizing circuit 10 is changed from the irradiation prohibition signal 22 to the irradiation permission signal 21 (T2), the coil conduction current control circuit 11a returns the current of the circular trim coil 7 to the original low value (see FIG. 2B), whereby the electron beam 9 is returned to the correct treatment passage, outputted to the outside (see FIG. 2C), and then used to irradiate the foci. This operation is continuously carried out during the period in which the irradiation permission signal 21 is outputted.

When the signal from the respiration synchronizing circuit 10 is changed from the irradiation permission signal 21 to the irradiation prohibition signal 22 (T3), the coil conduction current control circuit 11a increases again the current of the circular trim coil 7 (see FIG. 2B), considerably changes the passage of the electron beam 9 one more time, and causes the electron beam 9 to impinge upon the beam stopper portion 12 so that the electron beam is stopped from being outputted to the outside (see FIG. 2C). The intermittent irradiation will hereinafter be performed in synchronism with respiration by repeating the above-mentioned operations.

Incidentally, although the heat generated when the electron beam 9 impinges upon the beam stopper portion 12 is removed by a water-cooling apparatus which cools the wall surface of the extraction pipe 8, it is not preferable that the impingement of the electron beam 9 is concentrated on one portion because there is then the risk that such concentrated portion will be melted. In this case, when the electron beam 9 impinges upon the beam stopper portion 12, it is possible to avoid the electron beam 9 from impinging upon one portion concentrically by properly fluctuating the impingement portion with the beam passage change control circuit 11 (coil conduction current control circuit 11a). According to this technology, a temperature can be prevented from rising locally, the life span of the beam stopper portion 12 can be prolonged, and hence the apparatus can be improved in durability and made highly reliable. To be concrete, this can be realized in such a manner that a current value (high-level current value) of the circular trim coil 7 is controlled by the coil conduction current control circuit 11a so as not to fall within a constant value, i.e. so as to be slightly fluctuated during the period in which the irradiation prohibition signal 22 is outputted. The leading edge and the trailing edge of the current value generated during the period in which the irradiation prohibition signal 22 is outputted in FIG. 2B shows an example of the above control operation. The reason that the current value is fluctuated not in the form of simple concavity and convexity but in the sawtooth shape is such that the electron beam 9 scans the surface of the beam stopper portion 12 and the portions on which the electron beam 9 impinges are averaged on the surface of the beam stopper portion 12, thereby making it possible to efficiently prevent the temperature from rising locally.

It is frequently observed that the electron beam 9 is outputted to the outside during the period in which the irradiation prohibition signal 22 is outputted from the respiration synchronizing circuit 10. This is due to the fact that a current does not flow in the circular trim coil 7 when a cable 14 laid between the coil conduction current control circuit 11a and the circular trim coil 7 is disconnected or when the circular trim coil 7 and a connector are not connected satisfactorily. In such case, the interlock is energized to immediately stop the microtron from being operated. Specifically, when the current transformer 13 detects the electron beam during the period in which the irradiation prohibition signal 22 is outputted from the respiration synchronizing circuit 10, the respiration synchronizing circuit 10 outputs the interlock signal. This interlock signal is supplied to the accelerator control circuit 16 to immediately stop the electron emission operation of the electron gun 6 and the oscillation operation of the magnetron 6. Thus, the driving of the magnetron is stopped instantly.

While the present invention is applied to the microtron as described above, it is needless to say that the present invention is not limited thereto and may be applied to other irradiation apparatus such as a linear accelerator (lineac).

Figure 3:
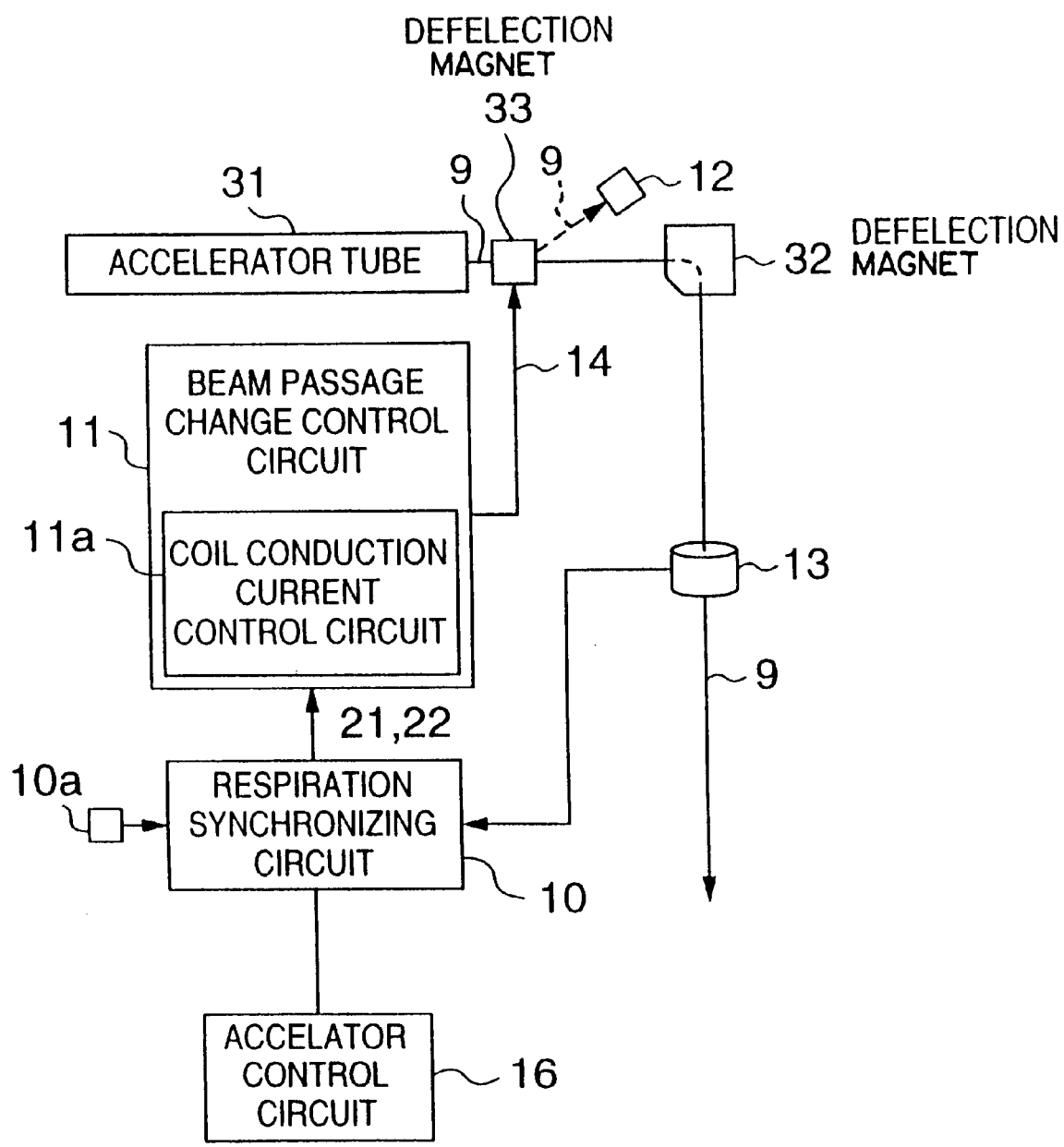
FIG. 3 is a block diagram showing a main portion of an irradiation apparatus according to another embodiment of the present invention.

FIG. 3 is a block diagram showing a main portion of one example in which the present invention is applied to the lineac. In FIG. 3, reference numeral 31 denotes an accelerator tube, and reference numerals 32, 33 denote deflection electromagnets. In FIG. 3, reference numerals identical to those of FIG. 1 denote the same or corresponding elements and parts. Incidentally, the deflection electromagnet 33 and the coil conduction current control circuit 11a constitute the beam passage change control circuit 11.

In this example, the deflection electromagnet 33 for performing the intermittent irradiation in synchronism with respiration is disposed between the accelerator tube 31 of the lineac and the deflection electromagnet 31, and this electromagnet is turned on and/off by the coil conduction current control circuit 11a.

Specifically, the coil conduction current control circuit 11a turns on (conducts) the deflection electromagnet 33 during the period in which the irradiation prohibition signal 22 is outputted from the respiration synchronizing circuit 10, whereby the passage of the electron beam 9 from the accelerator tube 31 is deflected from the correct treatment passage so that the electron beam is caused to impinge upon the beam stopper portion 12, thus resulting in the electron beam being prevented from being outputted to the outside. The energy of the electron beam 9 is consumed and absorbed when the electron beam impinges upon the beam stopper portion 12.

Also, when the signal from the respiration synchronizing circuit 10 is changed from the irradiation prohibition signal 22 to the irradiation permission signal 21, the coil conduction current control circuit 11a turns off (cuts off the current) the deflection electromagnet 33, returns the passage of the electron beam 9 to the correct treatment passage, and allow the electron beam to be outputted to the outside.

When the signal from the respiration synchronizing circuit 10 is changed from the irradiation permission signal 21 to the irradiation prohibition signal 22, the coil conduction current control circuit 11a again turns on (conducts) the deflection electromagnet 33, again deflects the passage of the electron beam 9 from the accelerator tube 31 toward the beam stopper portion 12 side, and causes the electron beam 9 to impinge upon the beam stopper portion 12, resulting in the electron beam being prevented from being outputted to the outside. Hereinafter, the intermittent irradiation will be performed in synchronism with respiration by repeating the above-mentioned operation.

Also, in the example of FIG. 3, the graphite or the like having high heat-resistance property and which generates less bremsstrahlung radiant rays is used as the beam stopper portion 12, the current transformer 13 detects that the electron beam 9 is outputted to the outside during the period in which the irradiation prohibition signal 22 is outputted from the respiration synchronizing circuit 10, and the accelerator control circuit 16 immediately stops the driving of the microtron similarly to the example illustrated in FIG. 1. Moreover, also in the example of FIG. 3, it may be possible to avoid the beam current 9 from concentrically impinging upon one portion of the beam stopper portion 12 by slightly changing the current generated when the deflection electromagnet 33 is turned on (conducted).

In the case of the lineac, there may be used proton rays, ions or the like instead of the electron beam. When X-rays are irradiated on the foci of the patient, electron beams are introduced into an X-ray generating target (not shown) to thereby generate X-rays. The X-rays are converged in the shape of beam and then irradiated on the foci.

When beams of radiant rays such as neutron or mesotron are irradiated on the foci of the patient, proton rays or ions are introduced into a target (not shown) which generates neutron, mesotron or the like, thereby generating neutron, mesotron or the like.

While the irradiation prohibition signal 22 is outputted when the irradiation permission signal 21 is outputted as described above, it is possible to determine based on the existence of the irradiation permission signal 21 whether or not the apparatus is set in the irradiation prohibition state.

It is to be understood that the invention is not limited to those precise embodiments and that various changes and modifications could be effected without departing from the spirit or scope of the invention as defined in the appended claims.

What is claimed is:

1. An irradiation apparatus for treating foci of a treated body by irradiating a charged particle beam or a radiation beam of high energy, comprising:

a respiration synchronizing circuit for detecting a respiration state of said treated body and outputting a radiation permission signal in synchronism with a rest period of said foci which are being moved by a respiration motion and a radiation prohibition signal in synchronism with a non-rest period of said foci; and a beam passage change control circuit for deflecting said beam from a correct passage, causing said beam to impinge upon a predetermined beam stopper portion during a period in which said radiation prohibition signal is outputted from said respiration synchronizing circuit and returning said beam to the correct passage during a period in which said radiation permission signal is outputted from said respiration synchronizing circuit.

2. An irradiation apparatus according to claim 1, further comprising an X-rays generating target for generating X-rays from said beams incident thereon.

3. An irradiation apparatus according to claim 1, further comprising a neutron generating target for generating neutron from said beams incident thereon.

4. An irradiation apparatus according to claim 1, further comprising a mesotron generating target for generating mesotron from said beams incident thereon.

5. An irradiation apparatus for treating foci of a treated body by irradiating a charged particle beam or a radiation beam of high energy, comprising:

a respiration synchronizing circuit for detecting a respiration state of said treated body and outputting a radiation permission signal in synchronism with a rest period of said foci which are being moved by a respiration motion; and a beam passage change control circuit for deflecting said beam from a correct passage, causing said beam to impinge upon a predetermined beam stopper portion during a period in which said radiation permission signal is not outputted from said respiration synchronizing circuit and returning said beam to the correct passage during a period in which said radiation permission signal is outputted from said respiration synchronizing circuit;

in which said beam passage change control circuit includes a circuit for properly fluctuating an impingement place when said beam is caused to impinge upon said beam stopper portion during a period in which said radiation permission signal is not outputted from said respiration synchronizing circuit.

6. An irradiation apparatus as claimed in claim 5, in which said beam passage change control circuit includes a circuit for increasing and/or decreasing a current flowing in a beam passage correction coil during a period in which said beam is caused to impinge upon said beam stopper portion.

7. An irradiation apparatus as claimed in claim 6, in which said beam passage change control circuit includes a circuit for changing the current flowing in said beam passage correction coil to a sawtooth current during a period in which said beam is caused to impinge upon said beam stopper portion.

8. An irradiation apparatus according to claim 5, further comprising an X-rays generating target for generating X-rays from said beam incident thereon.

9. An irradiation apparatus according to claim 5, further comprising a neutron generating target for generating neutron from said beams incident thereon.

10. An irradiation apparatus according to claim 5, further comprising a mesotron generating target for generating mesotron from said beams incident thereon.

* * * * *